United States Patent [19]
Hamamoto et al.

[11] Patent Number: 5,618,699
[45] Date of Patent: Apr. 8, 1997

[54] PLANT VIRUS VECTOR, PLASMID, PROCESS FOR EXPRESSION OF FOREIGN GENE AND PROCESS FOR OBTAINING FOREIGN GENE PRODUCT

[75] Inventors: Hiroshi Hamamoto, Tsukuba; Yoshinori Sugiyama, Odawara; Noriaki Nakagawa, Odawara; Eiji Hashida, Odawara; Suguru Tsuchimoto, Odawara; Noriyuki Nakanishi, Zama; Yuji Matsunaga, Osaka; Yoshimi Okada, Matsudo, all of Japan

[73] Assignee: Kanebo Limited, Tokyo, Japan

[21] Appl. No.: 313,127

[22] PCT Filed: Mar. 31, 1993

[86] PCT No.: PCT/JP93/00408

§ 371 Date: Nov. 30, 1994

§ 102(e) Date: Nov. 30, 1994

[87] PCT Pub. No.: WO93/20217

PCT Pub. Date: Oct. 14, 1993

[30] Foreign Application Priority Data

Mar. 31, 1992 [JP] Japan .................................. 4-108628
Jun. 22, 1992 [JP] Japan .................................. 4-188744
Dec. 8, 1992 [JP] Japan .................................. 4-351970

[51] Int. Cl.$^6$ .......................... C12N 15/40; C12N 15/62; C12N 15/82; C12N 15/83
[52] U.S. Cl. ...................... 435/69.7; 435/69.1; 435/70.1; 435/172.3; 435/235.1; 435/320.1; 536/23.72; 800/205; 800/DIG. 43; 800/DIG. 44
[58] Field of Search ................................ 435/69.1, 70.1, 435/172.3, 235.1, 320.1, 69.7; 536/23.72; 800/205, DIG. 43, DIG. 44

[56] References Cited

FOREIGN PATENT DOCUMENTS

WO8908145 9/1989 WIPO.

OTHER PUBLICATIONS

Skuzeski et al. 1991. J. Mol. Biol. 218:365–373.
Takamatsu et al. 1983. Nucleic Acids Research II(11): 3767–3778.
Ugaki et al. 1991. J. Gen. Virol. 72:1487–95.
Solis et al. 1990. Virology 177:553–558.
Isomura et al. 1991. J. Gen. Virol. 72:2247–2249.
Alonso et al. J. Gen. Virol. 72: 2875–2884.
Takamatsu et al, The EMBO Journal vol. 6, No. 2, pp. 307–311 (1987).
Saito et al, Virology 176, pp. 329–336 (1990).
Meshi et al, Proc. Natl. Acad. Sci. USA, vol. 83, pp. 5043–5047 (1986).
Ahlquist et al, Mol. Cell. Biol. vol. 4 No. 12, pp. 2876–2882 (1984).
Rosa, Cell. vol. 16 pp. 815–825 (1979).
Joshi et al, "Strategies for Expression of Foreign Genes in Plants—Potential Use of Engineered Viruses", *FEBS Letter*, 281(1,2):1–8 (1991).
Takamatsu et al, "Production of Enkephalin in Tobacco Protoplasts Using Tobacco Mosaic Virus RNA Vector", *FEBS Letter*, 269(1):73–76 (1990).
Skuzeski et al. 1990. Plant Mol. Biol. 15: 65–79.

*Primary Examiner*—David T. Fox
*Attorney, Agent, or Firm*—Sughrue, Mion, Zinn, Macpeak & Seas

[57] ABSTRACT

The present invention relates to a plant virus vector comprising a foreign gene linked downstream of a coat protein gene of tobacco mosaic virus via a nucleotide sequence which cause the readthrough, and a plasmid which is transcribed to provide the vector, as well as a process for expression of a foreign gene in a plant by inoculating the plant with the vector.

In addition, the present invention relates to a process for efficiently recovering a foreign gene product produced in a plant as virions.

25 Claims, 9 Drawing Sheets

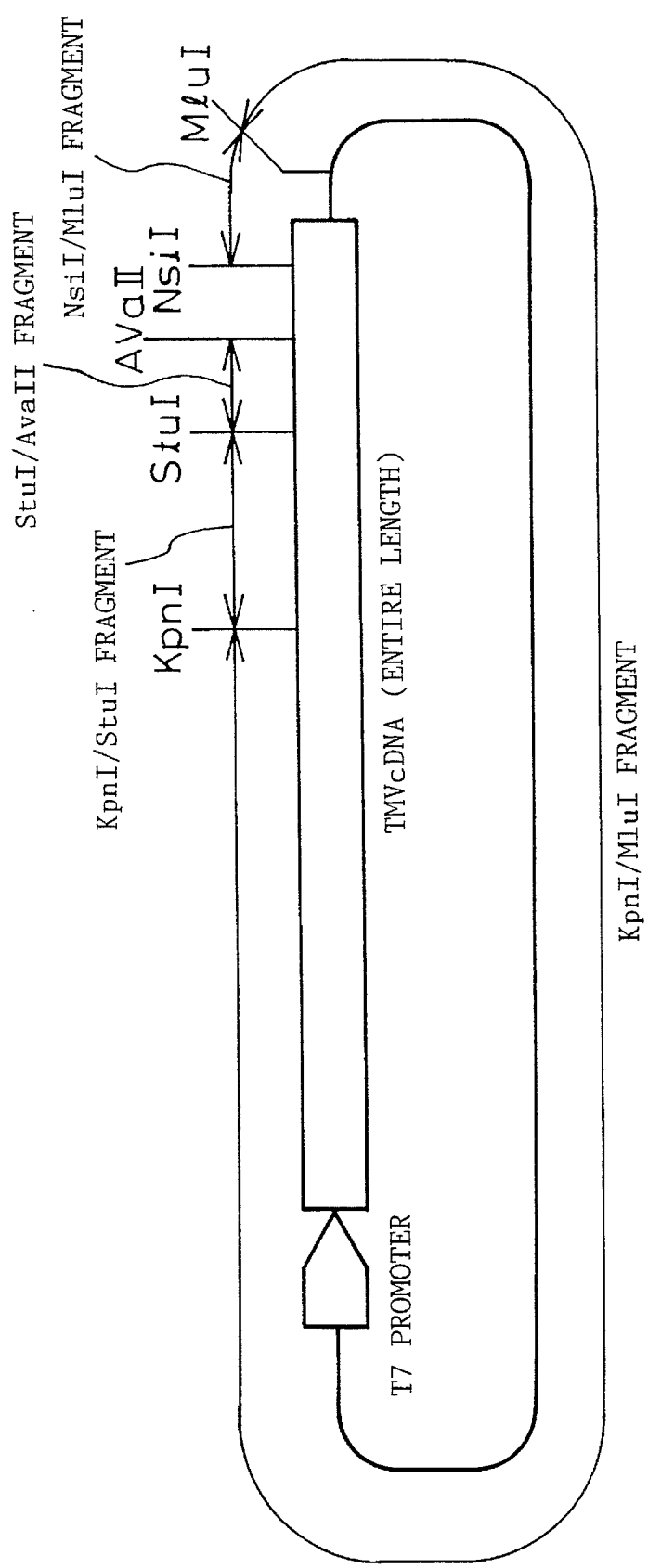

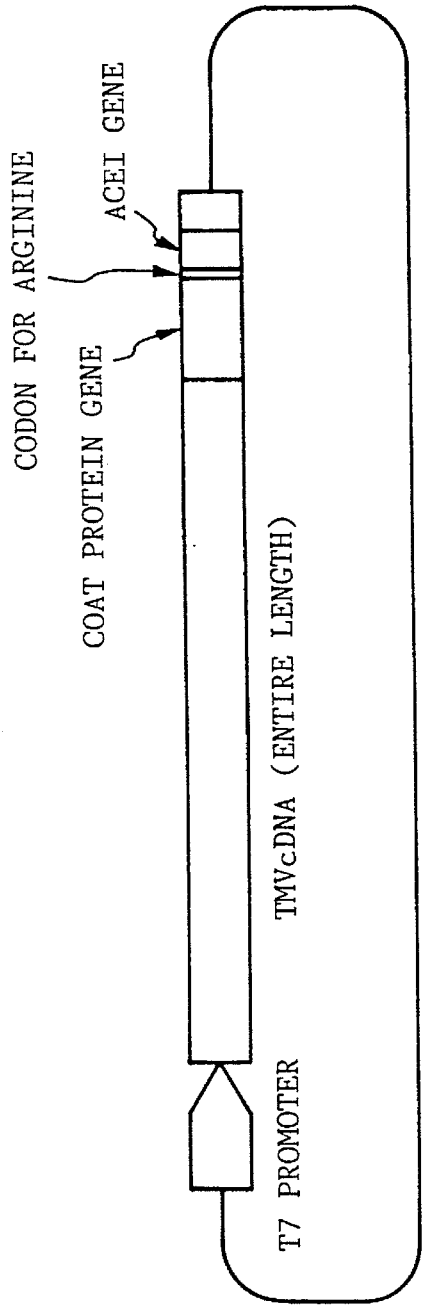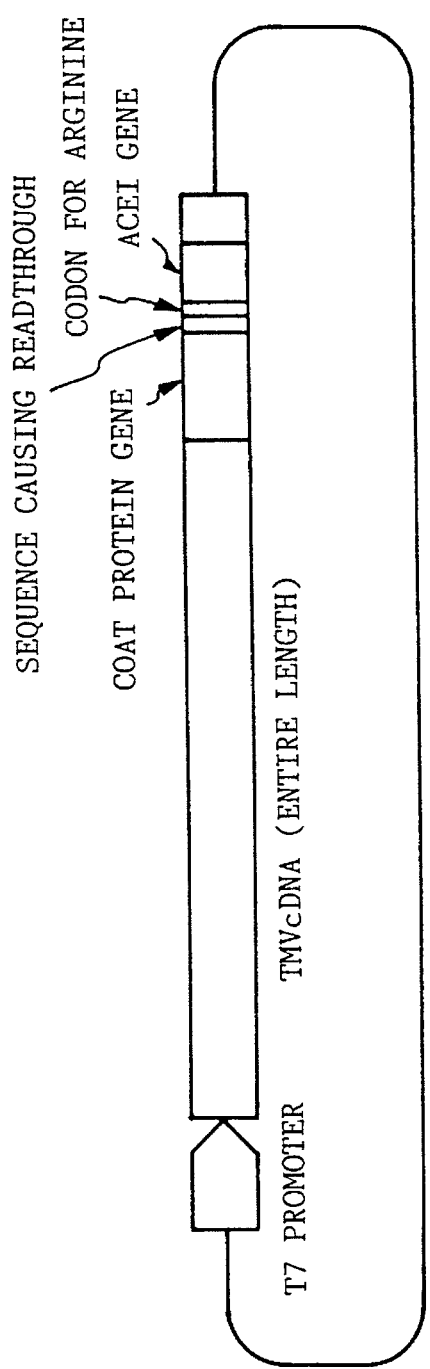

Fig.5

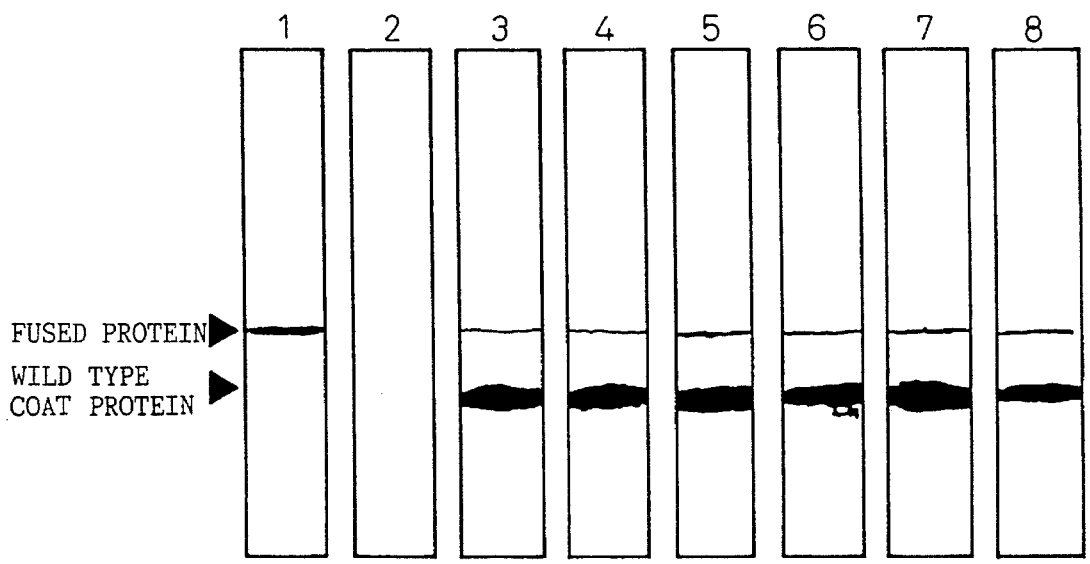

1 ... LEAF INFECTED WITH DIRECT JOINED TYPE
    VECTOR (COMPARATIVE EXAMPLE 1)
2 ... LEAF NOT INFECTED WITH DIRECT JOINED TYPE
    VECTOR (COMPARATIVE EXAMPLE 1)
3 ... LEAF INFECTED WITH READTHROUGH TYPE
    VECTOR (EXAMPLE 1)
4 ... LEAF NOT INFECTED WITH READTHROUGH TYPE
    VECTOR (EXAMPLE 1)
5 ... LEAF INFECTED WITH ONE NUCLEOTIDE-REPLACED
    READTHROUGH TYPE VECTOR (EXAMPLE 2)
6 ... LEAF NOT INFECTED WITH ONE NUCLEOTIDE-REPLACED
    READTHROUGH TYPE VECTOR (EXAMPLE 2)
7 ... LEAF INFECTED WITH THREE NUCLEOTIDE-REPLACED
    READTHROUGH TYPE VECTOR (EXAMPLE 3)
8 ... LEAF NOT INFECTED WITH THREE NUCLEOTIDE-
    REPLACED READTHROUGH TYPE VECTOR (EXAMPLE 3)

Fig.6

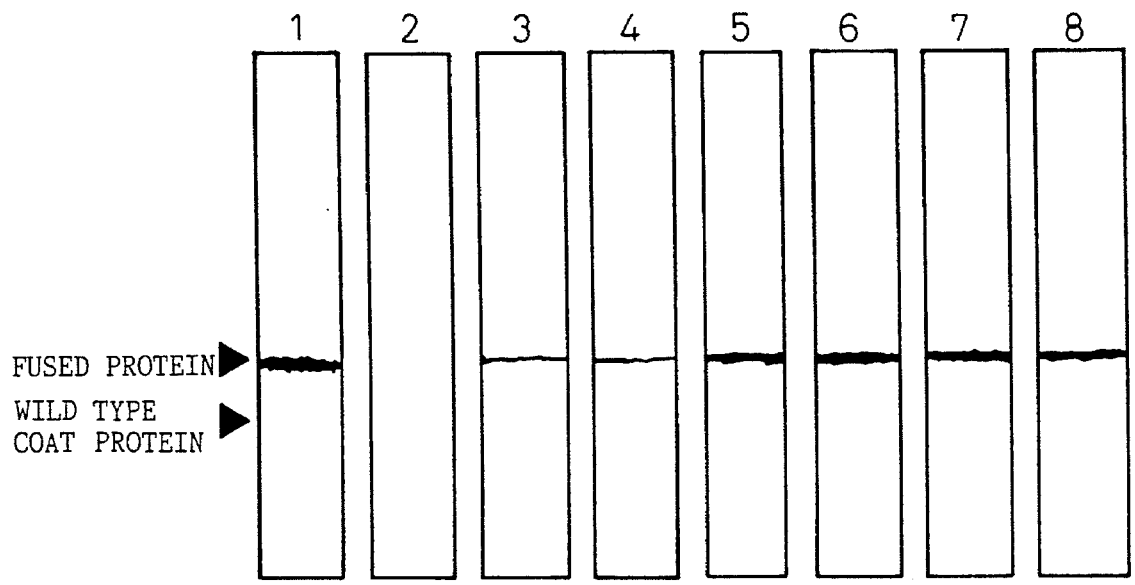

1 ... LEAF INFECTED WITH DIRECT JOINED TYPE
      VECTOR (COMPARATIVE EXAMPLE 1)
2 ... LEAF NOT INFECTED WITH DIRECT JOINED TYPE
      VECTOR (COMPARATIVE EXAMPLE 1)
3 ... LEAF INFECTED WITH READTHROUGH TYPE
      VECTOR (EXAMPLE 1)
4 ... LEAF NOT INFECTED WITH READTHROUGH TYPE
      VECTOR (EXAMPLE 1)
5 ... LEAF INFECTED WITH ONE NUCLEOTIDE-REPLACED
      READTHROUGH TYPE VECTOR (EXAMPLE 2)
6 ... LEAF NOT INFECTED WITH ONE NUCLEOTIDE-REPLACED
      READTHROUGH TYPE VECTOR (EXAMPLE 2)
7 ... LEAF INFECTED WITH THREE NUCLEOTIDE-REPLACED
      READTHROUGH TYPE VECTOR (EXAMPLE 3)
8 ... LEAD NOT INFECTED WITH THREE NUCLEOTIDE-
      REPLACED READTHROUGH TYPE VECTOR (EXAMPLE 3)

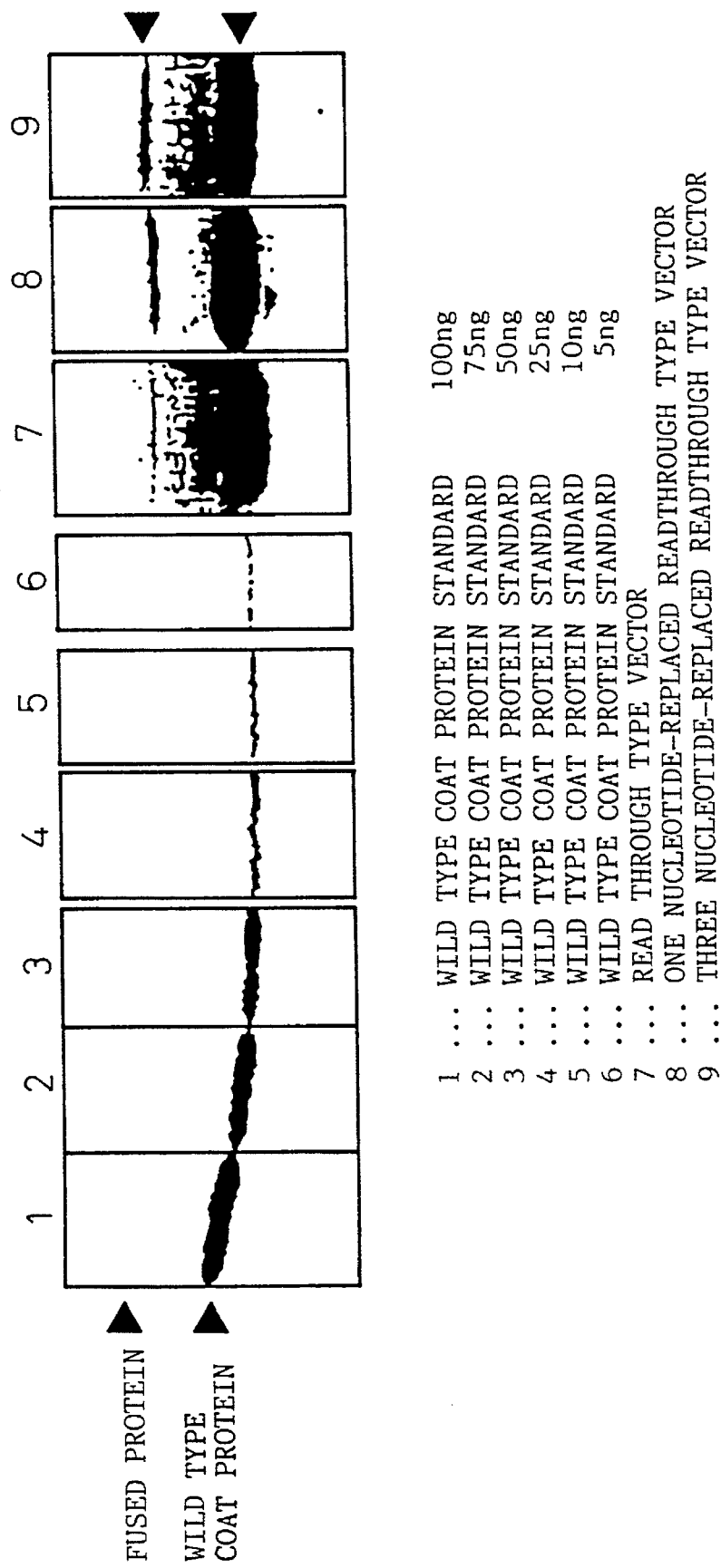

1 ... TOMATO FRUIT NOT INFECTED
2 ... TOMATO FRUIT INFECTED WITH THE PRESENT VECTOR

◀ FUSED PROTEIN
◀ WILD TYPE COAT PROTEIN

◀ FUSED PROTEIN
◀ WILD TYPE COAT PROTEIN

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
( A ) LENGTH: 66 base pairs
( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:1:

```
GACCTCTGCA  CCTGCATCTA  GATTCTTCGT  TGCTCCTTTT  CCTGAAGTAT    50

TCGGTAAGTA  AATGCA                                            66
```

( 2 ) INFORMATION FOR SEQ ID NO:2:

( i ) SEQUENCE CHARACTERISTICS:
( A ) LENGTH: 59 base pairs
( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:2:

```
TTTACTTACC  GAATACTTCA  GGAAAAGGAG  CAACGAAGAA  TCTAGATGCA    50

GGTGCAGAG                                                     59
```

( 2 ) INFORMATION FOR SEQ ID NO:3:

( i ) SEQUENCE CHARACTERISTICS:
( A ) LENGTH: 75 base pairs
( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:3:

```
GACCTCTGCA  CCTGCATCTT  AGCAATTAAG  ATTCTTCGTT  GCTCCTTTTC    50

CTGAAGTATT  CGGTAAGTAA  ATGCA                                 75
```

( 2 ) INFORMATION FOR SEQ ID NO:4:

( i ) SEQUENCE CHARACTERISTICS:
( A ) LENGTH: 68 base pairs
( B ) TYPE: nucleic acid
( C ) STRANDEDNESS: single
( D ) TOPOLOGY: linear ( i i ) MOLECULE TYPE: DNA (synthetic)

( x i ) SEQUENCE DESCRIPTION: SEQ ID NO:4:

```
TTTACTTACC  GAATACTTCA  GGAAAAGGAG  CAACGAAGAA  TCTTAATTGC    50

TAAGATGCAG  GTGCAGAG                                          68
```

( 2 ) INFORMATION FOR SEQ ID NO:5:

( i ) SEQUENCE CHARACTERISTICS:
( A ) LENGTH: 75 base pairs (B) TYPE: nucleic acid
(C) STRANDEDNESS: single
(D) TOPOLOGY: linear (ii) MOLECULE TYPE: DNA (synthetic)

(xi) SEQUENCE DESCRIPTION: SEQ ID NO:5:

```
GACCTCTGCA CCTGCATCAT AGCAATTAAG ATTCTTCGTT GCTCCTTTTC       50

CTGAAGTATT CGGTAAGTAA ATGCA                                  75
```

(2) INFORMATION FOR SEQ ID NO:6:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:6:

```
TTTACTTACC GAATACTTCA GGAAAAGGAG CAACGAAGAA TCTTAATTGC       50

TATGATGCAG GTGCAGAG                                          68
```

(2) INFORMATION FOR SEQ ID NO:7:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:7:

```
GACCTCTGCA CCTGCACAAT AGCAATTAAG ATTCTTCGTT GCTCCTTTTC       50

CTGAAGTATT CGGTAAGTAA ATGCA                                  75
```

(2) INFORMATION FOR SEQ ID NO:8:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:8:

```
TTTACTTACC GAATACTTCA GGAAAAGGAG CAACGAAGAA TCTTAATTGC       50

TATTGTGCAG GTGCAGAG                                          68
```

(2) INFORMATION FOR SEQ ID NO:9:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

```
Phe Phe Val Ala Pro Phe Pro Glu Val Phe Gly Lys
            5                   10
```

(2) INFORMATION FOR SEQ ID NO:10:

(i) SEQUENCE CHARACTERISTICS:
    (A) LENGTH: 7 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:10:

Ala Val Pro Tyr Pro Gln Arg
                     5

(2) INFORMATION FOR SEQ ID NO:11:

(i) SEQUENCE CHARACTERISTICS:
    (A) LENGTH: 6 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:11:

Thr Thr Met Pro Leu Trp
                     5

(2) INFORMATION FOR SEQ ID NO:12:

(i) SEQUENCE CHARACTERISTICS:
    (A) LENGTH: 5 amino acids
    (B) TYPE: amino acid
    (C) STRANDEDNESS: single
    (D) TOPOLOGY: linear (ii) MOLECULE TYPE: peptide (xi) SEQUENCE DESCRIPTION: SEQ ID NO:12:

Phe Phe Val Ala Pro
                 5

PLANT VIRUS VECTOR, PLASMID, PROCESS FOR EXPRESSION OF FOREIGN GENE AND PROCESS FOR OBTAINING FOREIGN GENE PRODUCT

FIELD OF THE INVENTION

The present invention relates to introduction of a foreign gene into a plant using a plant virus vector, improvement of plant properties and expression of a foreign gene throughout a whole plant, and a process for simply and efficiently obtaining a foreign gene product.

BACKGROUND OF THE INVENTION

It is known that plant viruses represented by tobamovirus, after infecting a plant, proliferate in the plant and rapidly spread systemically throughout the plant while producing viral coat protein in large amounts.

So far, some gene engineering systems for these plant viruses have been constructed and some attempts have been carried out to introduce a foreign gene into a plant using said systems. For example, there is a process wherein a coat protein gene is replaced with a foreign gene (Takamatsu et al, *EMBO J.*, 6:307–311 (1987)), and a process wherein a coat protein gene and a foreign gene are directly joined so as to produce a fused protein (Takamatsu et al, *FEBS Lett.*, 269:73–76 (1990)).

However, all of the plant viruses used in these known processes have a drawback in that they do not spread systemically in a plant (i.e., they do not have systemic infectivity), and thus, it is impossible to introduce a useful property and to produce a useful protein throughout a whole plant.

For a plant virus to exhibit systemic infectivity, particle formation with wild type coat protein is essential (Saito et al, *Virology*, 176:329 (1990)). As to existing plant virus vectors, since the coat protein is not produced (replacement-type vector), or the coat protein is in the form of a fused protein, resulting in a big change in properties (direct-joining type vector); then particles cannot be formed and systemic infectivity is not exhibited.

In addition, where existing plant virus vectors are used to express a foreign gene, it is very difficult to isolate and purify the foreign gene product from the plant into which the foreign gene was introduced.

The reason is that to establish (1) simple apparatus and economy, (2) high recovery, (3) high purity and (4) good reproduction, which are the goals of isolation and purification, a combination of operations, such as differential precipitation, desalting, concentration, and various chromatographies is essential; however, a series of these operations usually takes one-half to one month to complete, and they are often time- and labor-consuming. Even assuming these operations are simple and rapid, a plant includes proteins whose properties, such as molecular weight, isoelectric point, affinity to a solvent, are similar to those of the foreign gene product; and therefore it is difficult to prevent loss of the foreign gene product during the isolation and purification process. Thus, high recovery of the foreign gene product is not expected.

SUMMARY OF THE INVENTION

The purpose of the present invention is to provide plant virus vectors having the ability to systemically infect a whole plant; plasmids, which are transcribed to provide said plant virus vectors; and a process for expressing a foreign gene throughout a whole plant by inoculating said plant virus vector into a plant.

In addition, a process for simply and efficiently obtaining a foreign gene product produced in a plant is provided.

To accomplish the above-mentioned purposes, the present inventors use plant virus vector wherein a foreign gene is linked downstream of a coat protein gene of a plant virus via a nucleotide sequence that causes readthrough (Skuzeski et al, *J. Mol. Biol.*, 218:365–373 (1991)); a plasmid that is transcribed to provide said plant virus vector; and infection throughout a whole plant (systemic infectivity) by inoculating said plant virus vector into a plant so as to express the foreign gene throughout the whole plant. It was also found that introduction of a useful property into a whole plant and the production of a useful protein in a whole plant are possible, and thus, the present invention has been achieved.

In addition the present inventors found that when a foreign gene product is recovered from a plant, the foreign gene product can be easily and efficiently recovered as viral particles.

Prior to explaining the constituent features of the present invention, the terms used in the specification are explained as follows:

Plant virus vector: a replicable recombinant product obtainable by introducing a foreign gene into a DNA or RNA sequence in a plant virus.

Readthrough: In translation of an RNA to a protein, a phenomenon wherein the translation does not stop at a stop codon, and sometimes continues to the next stop codon. This readthrough phenomenon is caused by a nucleotide sequence near the stop codon.

Plant: in addition to an individual plant (a plant consisting of leaves, stem and roots); plant cells, callus, protoplast, as well as adventitious buds, adventitious roots and somatic embryos, derived from callus, are included, which are used as hosts for a plant virus.

Wild coat protein: A protein essential for formation of virions. Although it is usually called coat protein, in the present invention, to distinguish it from a coat protein in a fused protein, it is described as wild coat protein.

Fused protein: A protein wherein a foreign gene product is joined to the C-terminal of a coat protein, or a protein wherein a part of a coat protein is replaced with a foreign gene product.

Virion: A viral genome covered with a coat protein.

As plant viruses used in the present invention, there are mentioned a group belonging to DNA viruses, such as Caulimovirus and Geminivirus; and a group belonging to RNA viruses, such as Tobamovirus, Bromovirus and Cucumovirus. Particular virus species include Cauliflower mosaic virus belonging to Caulimovirus; Tomato golden mosaic virus belonging to Geminivirus; Tobacco mosaic virus belonging to Tobamovirus; Bromo mosaic virus belonging to Bromovirus; and Cucumber mosaic virus belonging to Cucumovirus.

Foreign genes used in the present invention include genes for peptides having a pharmacological or physiological activity; genes for proteins which provide stress resistance or pest resistance to a plant; and genes for proteins which change flower shape or color; more particularly, genes coding for enkephalins, calcitonins, corticotropins, human epidermal growth factor, and angiotensin converting enzyme inhibitor (ACEI) peptides having hypotensive action, as shown in the following Table 1.

TABLE 1

| | | |
|---|---|---|
| $CEI_{12}$: | Phe—Phe—Val—Ala—Pro—Phe—Pro—Glu—Val—Phe—Gly—Lys | (SEQ ID NO: 9) |
| $CEI_{87}$: | Ala—Val—Pro—Tyr—Pro—Gln—Arg | (SEQ ID NO: 10) |
| $CEI_6$: | Thr—Thr—Met—Pro—Leu—Trp | (SEQ ID NO: 11) |
| $CEI_5$: | Phe—Phe—Val—Ala—Pro | (SEQ ID NO: 12) |

These genes may be derived from genomic DNA and cDNA of organisms, as well as plasmid DNAs, although they can also be synthesized by a DNA synthesizer.

Nucleotide sequences used in the present invention, which cause readthrough, may be any nucleotide sequences which cause the readthrough phenomenon, and include, for example, naturally occurring nucleotide sequences, such as a nucleotide sequence encoding the 130/180K protein of tobacco mosaic virus, and those nucleotide sequences wherein a part of the nucleotide sequence is replaced with another nucleotide sequence.

Particularly, there are mentioned UAGCAAUUA present in the 130/180K dalton protein gene of tobacco mosaic virus, or a corresponding DNA type TAGCAATTA (wherein the underlined portions are a stop codon); UAACAAUUA (TAACAATTA) and UGACAAUUA (TGACAATTA) wherein the stop codon is replaced with another stop codon; and UAGCARYYA (TAGCARYYA) (wherein R represents A or G, Y represents C or U or T) wherein a portion other than the stop codon is replaced, although among them UAGCAAUUA (TAGCAATTA) is preferable because it has high readthrough efficiency.

Coat protein genes of plant viruses used in the present invention include naturally occurring genes, genes wherein a part of the naturally occurring gene is deleted, and genes wherein a part of the naturally occurring gene is replaced with another nucleotide sequence, and particularly, coat protein genes whose nucleotide just before the readthrough-causing nucleotide sequence is A, are preferable because of their high readthrough efficiency.

Examples of nucleotide replacement sequences are, in the case of tobacco mosaic virus, replacement of the U(T) of the 3'-terminus of the coat protein gene with A, and replacement of the UCU(TCT) of the 3'-terminus with CAA. These replacements are preferable in that they remarkably increase readthrough efficiency.

Plasmids used in the present invention include, in the case where the plant virus is an RNA virus, pLFW3 (Meshi et al, *Proc. Natl. Acad. Sci. USA*, 83:5043 (1986)) having a PM promoter (Ahlquist et al, *Mol. Cell. Biol.*, 4:2876–2882 (1984)) as a promotor for in vitro transcription; pTLW3 (Meshi et al, In: *Genetic Engineering with Plant Viruses*, Wilson, T. M. A. and Davis, J. W. (Eds)., CRC, Florida, U.S.A., page 154 (1992)) having a T7 promotor (Rosa, *Cell*, 16:815–825 (1979)), although in the case where the plant virus is a DNA virus, plasmids not having a promotor for in vitro transcription can be used.

Plant virus vectors, in the case where the virus is an RNA virus, can be constructed, for example, as follows.

First, cDNA of a plant RNA virus is introduced downstream of a promotor of a plasmid having a promotor for in vitro transcription. Next, according to a conventional procedure used in gene engineering, a desired foreign gene is introduced downstream of a coat protein gene of the plant virus via a readthrough-causing nucleotide sequence.

In this case, it is preferable to insert a nucleotide sequence encoding amino acid(s) recognized by protease between the readthrough-causing nucleotide sequence and the foreign gene, so that a foreign gene-derived protein (or peptide) can be easily isolated. Amino acids recognized by protease include, for example, arginine and lysine (cleaved with trypsin), phenylalanine and tyrosine (cleaved with chymotrypsin), as well as methionine (chemically cleaved with cyanogen bromide).

Next, RNA is prepared from the plasmid as constructed above by in vitro transcription, and is used as a plant virus vector. In addition, the present plant virus vector may be those prepared by forming particles with the coat protein of a wild type virus (plant virus vector particles).

Where the virus is DNA, the DNA of the virus is directly introduced into a plasmid for gene engineering. A plant virus vector can be prepared by cutting out the DNA virus portion from the engineered plasmid, or a similar method.

The plant virus vector, obtained as described above, can be easily infected into a plant in the form of RNA or DNA, or preferably in the form of a virion if it is RNA, for example, by rubbing it on a leaf with carborundum, or by spraying it on a leaf as a mixture with carborundum.

In this case, the plants may be any plant which the present plant virus vector can infect. For example, where the virus used as a vector is Tobacco mosaic virus, plants belonging to the family Solanaceae, such as tobacco, tomato, red pepper, may be used; where the virus is Brome mosaic virus, plants belonging to the family Graminales, such as barley and wheat, may be used; where the virus is cauliflower mosaic virus, plants or cultured cells belonging to the family Cruciferae, such as cauliflower and turnip, may be used.

An infected plant simultaneously produces both the wild type coat protein and a fused protein throughout the whole plant. Namely, a foreign gene product is produced as a fused protein.

In addition, it can be found by isolating plant virons from infected plants and purifying and lysing the plant virions that both the wild type coat protein and the fused protein are used for formation of virons.

This fact means that the fused protein is also used for formation of virions in the copresence of the wild type and is obtained as a fused protein by recovering the plant virions from the plant. The fused protein thus obtained may be cleaved by an appropriate means to obtain a desired foreign gene product.

The recovery of virions does not require expensive reagents, is not time-consuming, and can be finished in approximately one day by using centrifugation. In addition, centrifugation is highly reproducible, and the purity of the virions obtained is high.

Since the present plant virus vector has a nucleotide sequence which causes readthrough, it simultaneously produces both a wild type coat protein and a fused protein (i.e., a fused protein comprising a desired protein or peptide derived from a foreign gene and the coat protein). Therefore, virions normally result in systemic infection and expression of the foreign gene throughout a whole plant.

In addition, according to the present invention, a foreign gene product with high purity can be reproducibly, easily and cheaply isolated and purified.

BRIEF DESCRIPTION OF THE DRAWINGS

FIG. 3 shows, in plasmid pTLW3, the positions of DNA fragments used for construction of plasmids in the Examples and Comparative Examples.

FIGS. 4(a)–4(b.) FIG. 4(a) shows the plasmid constructed in Comparative Example 1 and 4(b) shows the plasmid constructed in Example 1.

FIG. 5 is a diagrammatic sketch that shows the presence or absence of the virus vector in infected and non-infected leaves in experiments infecting individual plants, carried out in Comparative Example 1 and Examples 1 to 3.

FIG. 6 is a diagrammatic sketch that shows the presence or absence of ACEI in an infected leaf and a non-infected leaf, in experiments infecting an individual plant, carried out in Comparative Example 1 and Examples 1 to 3.

FIG. 7 is a diagrammatic sketch that shows the ability of the present readthrough vectors (Examples 1 to 3) to produce a fused protein.

DETAILED DESCRIPTION OF THE INVENTION

Figure 1:
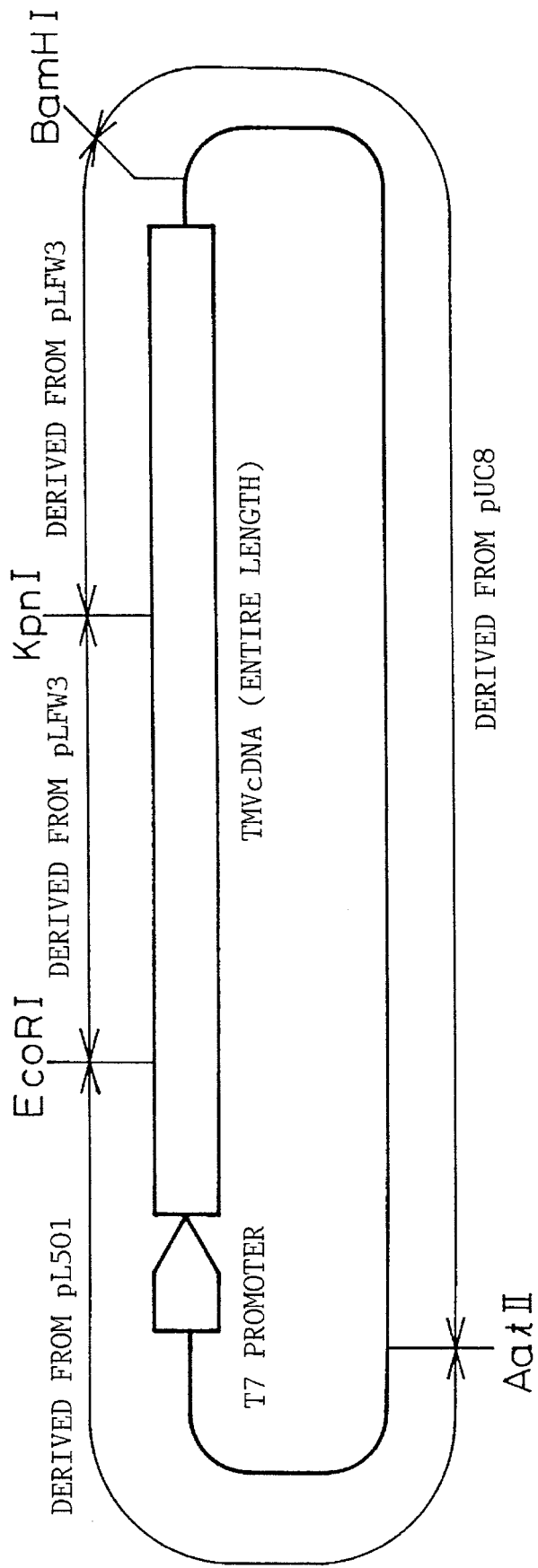
FIG. 1 shows plasmid pTLW3.

The present invention is further explained in detail in the following Examples. Note that plasmid pTLW3 used in the Examples is shown in FIG. 1.

EXAMPLES 1 TO 3 AND COMPARITIVE EXAMPLE 1

Figure 2:
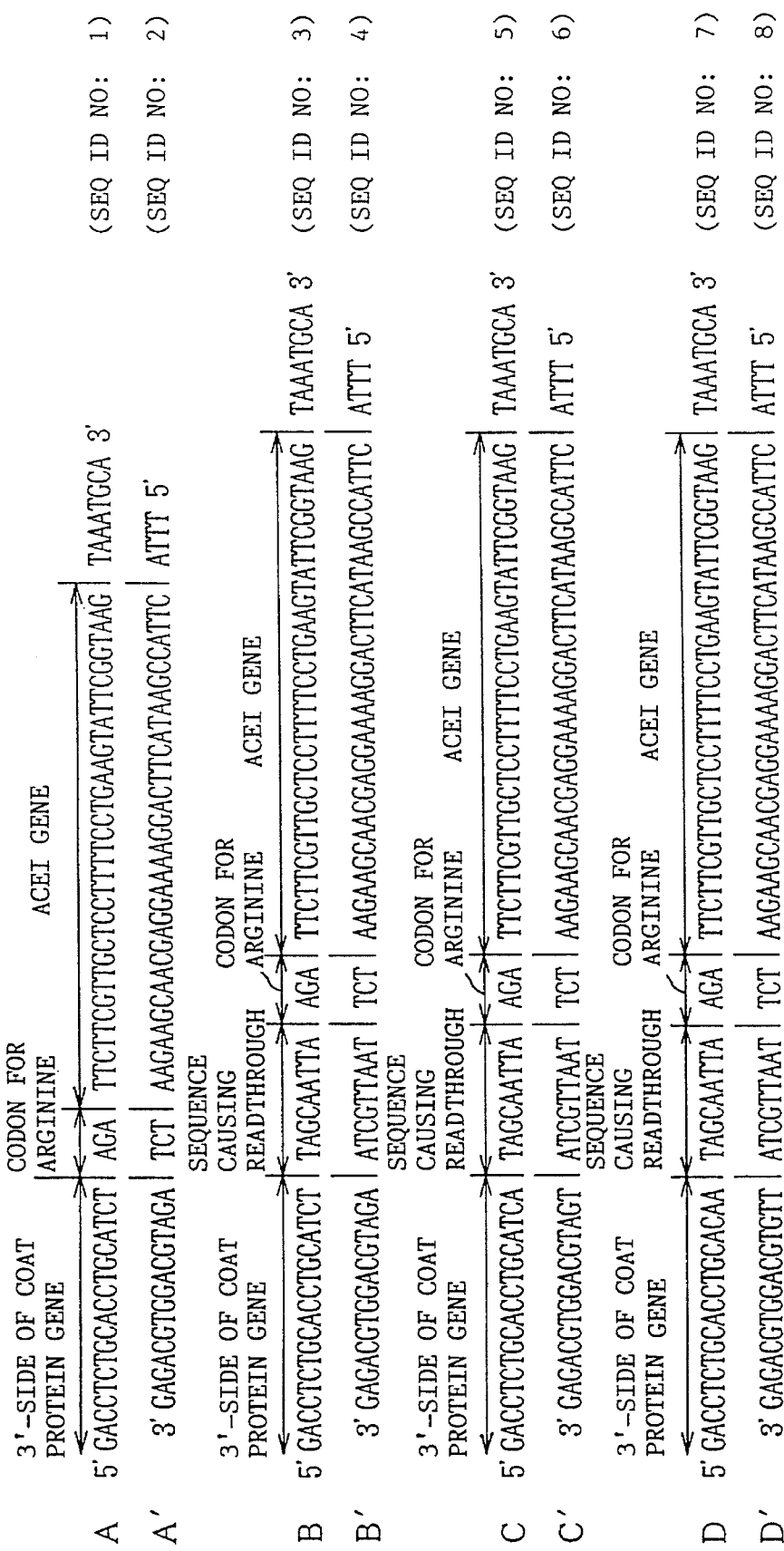
FIG. 2 shows a nucleotide sequence of a synthetic DNA used for construction of plant virus vectors in the Examples and Comparative Examples (A and A' were used in Comparative Example 1; B and B' were used in Example 1; C and C' were used in Example 2; and D and D' were used in Example 3).

1. Construction of Template Plasmid Incorporating ACEI Gene Sequence (1) Construction of Synthetic DNAs Comprising ACEI Gene Sequence Eight synthetic DNAs shown in FIG. 2 were prepared in 0.2 μmol scale using a 380A Type DNA synthesizer from Applied Biosystems, Inc. (ABI Inc.). A and A' were used for a conventional, direct, joined type vector (Comparative Example 1), B and B' were used for a readthrough type vector (Example 1), C and C' were used for a readthrough type vector wherein one nucleotide at the 3-terminus of a coat protein gene has been replaced (Example 2), and D and D' were used for a readthrough type vector where three nucleotides at the 3'-terminus of a coat protein gene were replaced (Example 3). All the vectors contain a sequence coding for an arginine at the 5'-side of an ACEI gene sequence so that an ACEI peptide can be isolated from an expressed fused protein by trypsin digestion. The synthesized DNAs were purified using an OPC cartridge from ABI Inc.

(2) Phosphorylation and Annealing of Synthetic DNAs

The DNAs synthesized in (1) above were adjusted to a concentration of 0.1 μg/μl, phosphorylated with 0.2 mM ATP, purified by treatment with phenol and washed with ethyl ether. The purified DNA was adjusted to a concentration of 0.02 μg/μl, and A and A', B and B', C and C', as well as D and D' were mixed, and each mixture was incubated at 65° C. for 5 minutes. After the incubation, the mixture was allowed to gradually cool to a room temperature for annealing.

(3) Preparation of Fragments for Construction of Plasmids

The plasmid pTLW3 shown in FIG. 1, which was constructed according to published literature (Meshi (1992), supra), was digested with a combination of restriction enzymes, shown in Table 2, to prepare fragments having different sizes. Note, the relationship between the fragments in pTLW3 is shown in FIG. 3.

TABLE 2

| KpnI/MluI Fragment | 7.1 kbp |
|---|---|
| KpnI/StuI Fragment | 1.2 kbp |
| StuI/AvaII Fragment | 0.56 kbp |
| NsiI/MluI Fragment | 0.2 kbp |

After separation by agarose electrophoresis, each fragment was prepared. using a GENE CLEAN kit (BIO 101), according to the instructions attached to the kit.

Among the above-mentioned fragments, the KpnI-MluI 7.1 kbp fragment was dephosphorylated at its end by alkaline phosphatase treatment, and used in the following reaction.

(4) Construction and Preparation of Plasmid

Each of 4 solutions of the annealed synthetic DNAs prepared in (2) above was reacted with a solution of 4 DNA fragments derived from pTLW3 prepared in (3) above respectively at 15° C. for 15 hours in the following composition so as to construct 4 plasmids. Among the plasmids thus obtained, two plasmids are shown in FIG. 4 (a: Comparative Example 1; and b: Example 1).

TABLE 3

| Solution of annealed synthetic DNA | (0.02 μg/μl) | 1.0 μl |
|---|---|---|
| KpnI/MluI Fragment | (0.001 μg/μl) | 9.0 μl |
| KpnI/StuI Fragment | (0.01 μg/μl) | 1.5 μl |
| StuI/AvaII Fragment | (0.015 μg/μl) | 0.5 μl |
| NsiI/MluI Fragment | (0.005 μg/μl) | 0.5 μl |
| × 10 binding buffer | | 1.5 μl |
| T4 Ligase [Takara Shuzo 350 Units/μl] | | 1.0 μl |
| Total | | 15.0 μl |

Note, the composition of the ×10 binding buffer is shown in Table 4.

TABLE 4

| Composition of × 10 binding buffer | |
|---|---|
| Tris-HCl (pH = 7.6) | 660 mM |
| MgCl$_2$ | 66 mM |

TABLE 4-continued

| Composition of × 10 binding buffer | |
| --- | --- |
| DTT | 100 mM |
| ATP | 1 mM |

The reaction mixture as such was used to transform competent cells of *E. coli* HB101 (Takara Shuzo), and colonies resistant to carbenicilin were selected. A desired plasmid was extracted and purified from *E. coli* cells of selected colonies.

2. Construction of Plant Virus Vectors by in Vitro Transcription

Four plasmids constructed in (1) above (i.e., a plasmid having a sequence of a conventional vector, and plasmids having a sequence of a vector of the present invention) were digested with a restriction enzyme, purified by phenol treatment and ethanol precipitation, and used as template DNAs. In vitro transcription reaction was carried out using the template DNA in the reaction system shown in Table 5, at 37° C. for 2 hours, to construct four plant virus vectors (RNA). The plant virus vectors (RNA) thus constructed were purified by phenol treatment and ethanol precipitation.

TABLE 5

| | |
| --- | --- |
| 1M Tris-HCl (pH = 8.0) | 4 µl |
| 1M MgCl$_2$ | 2 µl |
| 1M DTT | 1 µl |
| 10 mg/ml BSA | 1 µl |
| 100 mM ATP | 1 µl |
| 100 mM UTP | 1 µl |
| 100 mM CTP | 1 µl |
| 10 mM GTP | 2 µl |
| 10 Mm CAP | 20 µl |
| Template DNA (0.5 mg/ml) | 10 µl |
| T7 Polymerase [Takara Shuzo 50 Units/µl] | 1 µl |
| RNase Inhibitor [Takara Shuzo 50 Units/µl] | 1 µl |
| H$_2$O | 55 µl |
| Total | 100 µl |

The plant virus vector (RNA) prepared as above and the wild type coat protein of tobacco mosaic virus purified according to a known procedure (Frankel-Contrat, *Virology*, 4:1–4 (1957)), were reacted in the composition shown in Table 6, at 20° C. for 15 hours to form virions artificially in vitro. The reaction mixture as such was used as the plant virus vector particle solution.

TABLE 6

| | | |
| --- | --- | --- |
| Plant virus vector (RNA) | (0.3 µg/µl) | 8 µl |
| Wild type coat protein | (10 µg/µl) | 10 µl |
| 0.2M Phosphate buffer | (pH = 7.0) | 18 µl |

3. Introduction of Foreign Gene into Individual Plant by Inoculation of Plant Virus Vector Particles The solution of the plant virus vector particles prepared in the above-mentioned 2) was diluted 100 fold with 10 mM phosphate buffer (pH 7.0), and 100 µl of the diluted solution was rubbed on each leaf of a 6 week old *Nicotiana tabacum* cv. Samsun seedling using carborundum (Nakarai Tesk, Carborundum, 600 mesh).

4. Confirmation of Replication of Plant Virus Vector in Individual Plant and Movement to Upper Leaves (1) Preparation of Sample 15 days after the plants' infection with plant virus vector particles, 10 mg of sections of infected leaf and non-infected leaves from the same individual plant were cut off. To each leaf section, 50 µl of an SDS sampling buffer having the composition shown in Table 7 was added, and after homogenizing, the homogenate was treated at 100° C. for 3 minutes. After cooling, the homogenate was centrifuged at 12,000 rpm for 5 minutes, and the supernatant was used as an SDS-protein sample.

TABLE 7

| Composition of SDS sampling buffer | |
| --- | --- |
| Tris-HCl (pH = 6.8) | 120 mM |
| SDS | 4% |
| 2-Mercaptoethanol | 10% |
| Glycerol | 20% |
| BPB | 0.002% |

(2) Detection of Plant Virus Vector in Sample

The presence or absence of plant virus vector was determined by the presence or absence of wild type coat protein and a fused protein. One µl of the SDS-protein sample prepared in the above-mentioned (1) was subjected to SDS-PAGE (12.5% polyacrylamide gel) to separate proteins. The separated proteins were transferred from the gel to a PVDF membrane by electric blotting. Next, an anti-tobacco mosaic virus rabbit serum was diluted 64,000 fold with TBS buffer [20 mM Tris-HCl (pH 7.6) and 137 mM NaCl] to obtain a primary antibody staining solution, and antibody staining was carried out using a rabbit antibody blotting detection kit (Amersham) according to the instructions attached to the kit. A result is shown in FIG. 5.

Although a conventional type plant virus vector producing a fused protein alone (Comparative Example 1) was detected in an infected leaf, movement to non-infected leaves was not observed (see FIG. 5, lanes 1 and 2).

On the other hand, the present plant virus vector, into which a readthrough sequence was introduced so that both the wild type coat protein and a fused protein are simultaneously produced (see Examples 1 to 3), was detected in both the infected and non-infected leaves, which confirms that the vector was spread from one leaf to another leaf within the plant (i.e., it had systemic infectivity) (see FIG. 5, lanes 3 to 8).

5) Confirmation of Production of ACEI in Plant

According to the same procedures as described in the above-mentioned 4), the sample of 4) was subjected to electrophoresis and transferred to the membrane, and antibody staining was carried out, using an anti-ACEI rabbit serum diluted 128,000 fold with TBS buffer as a primary antibody staining solution.

The result is shown in FIG. 6. Thus, it was confirmed that the conventional type plant virus vector produced ACEI in the form of a fused protein only in an infected leaf, and the present plant virus vectors produce ACEI in the form of a fused protein in both infected non-infected leaves.

Comparison of Fused Protein Productivity of Plant Virus Vectors

The same procedure as described in 4)(2) was carried out to compare the fused protein productivity of plant virus vectors of Examples 1 to 3.

In this case, samples to be subjected to SDS-PAGE were extracted from infected leaves, and the amount of the sample was adjusted to correspond to 0.2 mg of a live leaf. In addition, as a standard, 100, 75, 50, 25, 10, and 5 ng of wild type coat protein of tobacco mosaic virus was simultaneously subjected to SDS-PAGE. Similar to 4)(2) above, detection was carried out by antibody staining with anti-tobacco mosaic virus rabbit serum. The result is shown in FIG. 7.

When the amount of fused protein produced by each vector was calculated by comparing the color densities of bands in FIG. 7, the vector of Example. 1 produced 0.025 mg fused protein per 1g tobacco leaf, and the vectors of Examples 2 and 3 produced 0.25 mg fused protein per 1 g tobacco leaf. From this result, it was found that replacement of U with A, or UCU with CAA at the 3'-terminus of the coat protein gene enhances the efficiency of the readthrough, and increases fused protein productivity by 10 times.

EXAMPLE 4

A solution of the present plant virus vector particles having the ACEI gene sequence constructed in Example 1 was infected into a leaf of a 6 month old mini tomato plant [Sugarlamp purchased from SAKATA NO TANE] grown from seed. The infection was carried out as in Example 1. After 14 days, tomato fruit was harvested, and the ACEI in a protein sample extracted from the tomato fruit was detected using an anti-ACEI antibody according to the same procedure as described in Example 1. The result is shown in FIG. 8.

Figure 8:
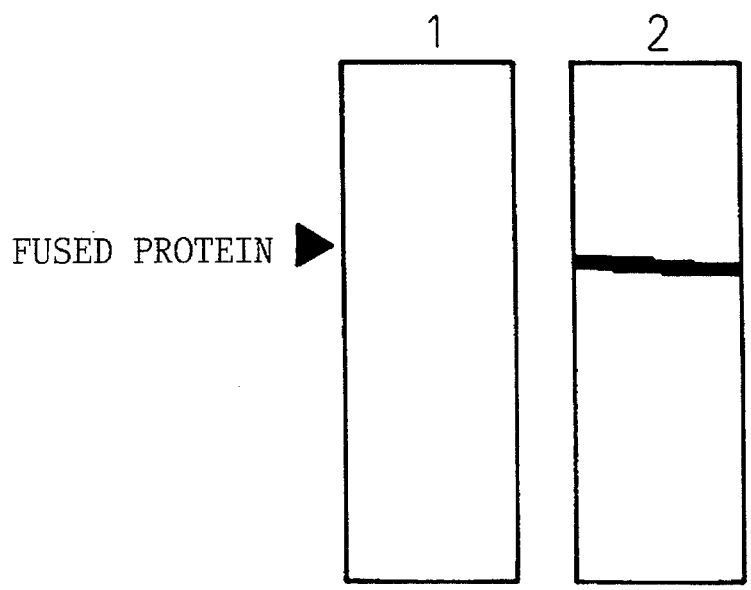
FIG. 8 is a diagrammatic sketch that shows the presence or absence of ACEI in a tomato fruit in an experiment infecting a mini tomato plant, carried out in Example 4.

As can be seen from FIG. 8, ACEI was produced in the tomato fruit.

It is expected that the tomato fruit produced contains a large amount of ACEI which exhibits hypotensive action by oral uptake.

EXAMPLE 5

1) Introduction of Foreign Gene into Plant by Inoculation of Plant Virus Vector

A solution of the present plant virus vector particles having ACEI gene sequence constructed in Example 2 was infected to a leaf of a 6 week old *Nicotiana tabacum* cv. Samsun seedling. The infection was carried out as in Examples 1 or 2.

Recovery of Plant Virions from Plant Incorporating a Foreign Gene 1 to 2 months after the infection, virions were purified from 10 g of leaves of the infected plant.

More specifically, the following procedures were carried out. Non-infected leaves of the infected tobacco plant were frozen and disrupted with a mixer. Next, to the disrupted non-infected leaves was added the same weight of 0.1M phosphate buffer (pH 7.0) containing 0.1% thioglycolic acid, and after homogenizing the mixture, the homogenate was centrifuged at a low temperature and at a low speed (8000× g, 10 minutes). The precipitate was discarded, and to the supernatant, was added 2M sodium chloride solution in an amount of 0.06 volume relative to the volume of the supernatant, and 20% polyethylene glycol in an amount of 0.2 volume relative to the volume of the supernatant, and the mixture was allowed to stand on ice for one hour.

Next, the mixture was centrifuged at low speed to recover the precipitate. The precipitate was thoroughly dispersed in distilled water, and a differential centrifugation comprising low speed centrifugation and high speed centrifugation (100,000×g, 50 minutes) was repeated twice. The precipitate from the final centrifugation was suspended in distilled water to obtain the virions.

The concentration of the virions was calculated as 10 mg/ml from absorbance at a wavelength of 280 nm. The isolation and purification procedure described above took about one day.

3. Evaluation of the Purity of the Virions

To 5 µl of the virions was added 5 µl of an SDS sampling buffer having the composition shown in Table 7, and after treating at 100° C. for 5 minutes, the mixture was used as an SDS-protein sample. Two µl of the SDS-protein sample was subjected to SDS-PAGE (12.5% polyacrylamide gel), and the gel was stained with Coomassie Brilliant Blue, decolored with 7.5% acetic acid/5% methanol, and dried. The result is shown in FIG. 9.

Figure 9:
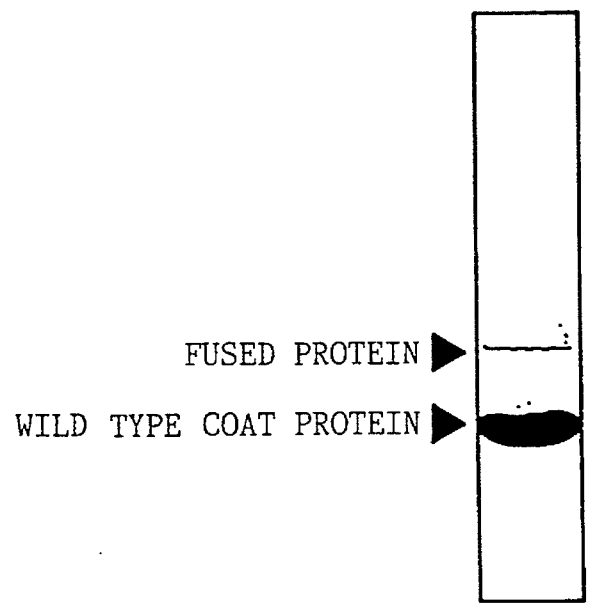
FIG. 9 is a diagrammatic sketch that shows the purity of recovered virions carried out in Example 5.

As can be seen from FIG. 9, only the wild type coat protein and the fused protein were detected, and other proteins derived from the plant were almost completely eliminated.

4) Detection of Fused Protein in Virions

An SDS-protein sample was prepared according to the same procedure as described in 3) above, and diluted 10 fold, and 2 µl of the diluted sample was subjected to SDS-PAGE (12.5% polyacrylamide gel) to separate proteins. The separated proteins were transferred from the gel to a PVDF membrane by electro blotting.

Figures 10A, 10B:
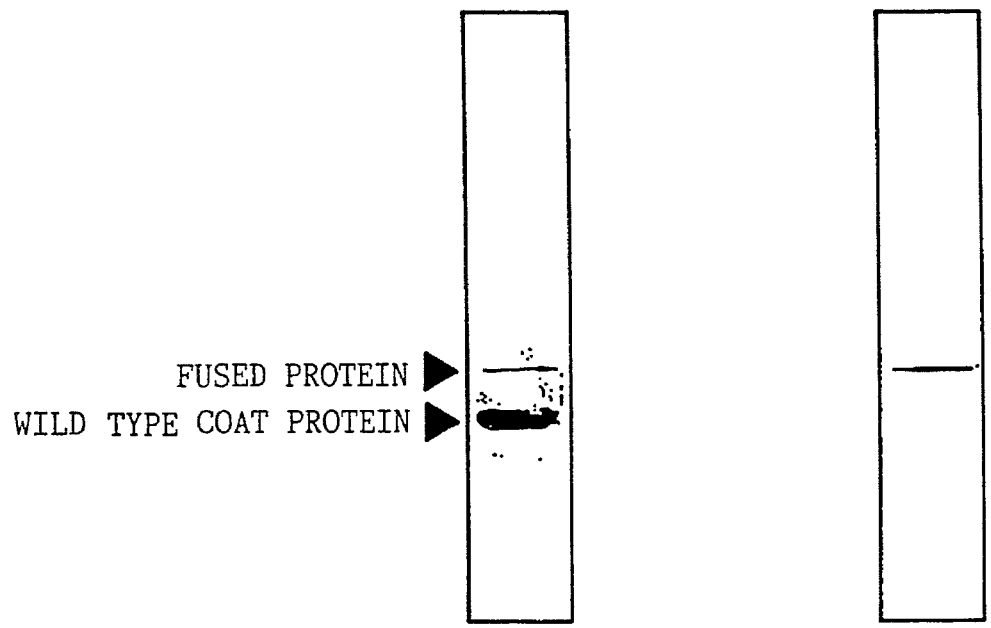
FIGS. 10(a)–10(b) are diagrammatic sketches that represent the presence or absence of a fused protein and an ACEI peptide in virions obtained in an experiment recovering virions, carried out in Example 5; 10(a) shows the result of antibody staining with anti-TMV rabbit serum, and 10(b) shows the result of antibody staining with anti-ACEI rabbit serum.

Next, antibody staining was carried out using an anti-TMV rabbit serum or anti-ACE1 rabbit serum as a primary staining solution, and using a rabbit antibody blotting detection kit (Promega) according to the instructions attached to the kit. The result is shown in FIGS. 10(*a*) and (*b*).

The ratio of fused protein and wild type coat protein incorporated into the virions was about 1:20, and the ratio substantially conformed to that in proteins isolated and purified from the plant. This fact shows that the fused protein was efficiently incorporated into the virions.

In addition, since the virions derived from non-infected leaves, contained the fused protein, it was found that by using a readthrough vector, virions containing a fused protein can be recovered from the whole plant.

INDUSTRIAL APPLICABILITY

As can be seen from the above, since the present plant virus vectors provide systemic infectivity, introduction of a desired property into a plant and the production of a foreign gene product in a whole plant are possible.

In addition, according to the present process, a foreign gene product with high purity can be reproducibly, cheaply and easily isolated and purified.

We claim:

1. A plant virus vector comprising a viral assembly origin and a foreign protein gene linked downstream of a coat protein gene of a Tobamovirus via a nucleotide sequence of a Tobamovirus which causes readthrough, such that upon expression of the vector in a plant, the coat protein and a fusion protein of the coat protein and the foreign protein are systemically produced in the plant.

2. The plant virus vector according to claim 1, wherein part of the coat protein gene is lacking or replaced.

3. The plant virus vector according to claim 1, wherein the nucleotide sequence which causes readthrough is UAGCAAUUA or the corresponding DNA sequence TAGCAATTA, UAACAAUUA or the corresponding DNA sequence TAACAATTA, UGACAAUUA or the corresponding DNA sequence, TGACAATTA, or UAGCARYYA or the corresponding DNA sequence TAGCARYYA, wherein the italicized lettering indicates a stop codon, R is A or G, and Y is C, U or T.

4. A plasmid comprising the plant virus vector according to claim 1.

5. The plasmid according to claim 4, wherein the nucleotide sequence which causes readthrough is UAGCAAUUA or the corresponding DNA sequence TAGCAATTA, UAACAAUUA or the corresponding DNA sequence TAACAATTA, UGACAAUUA or the corresponding DNA sequence TGACAATTA, or UAGCARYYA or the corresponding DNA sequence TAGCARYYA, wherein italicized lettering indicates a stop codon, R is A or G, and Y is C, U or T.

6. The plasmid according to claim 4, wherein said plasmid comprises cDNA to said Tobamovirus and a promoter for transcribing said cDNA upstream from said cDNA.

7. The plasmid according to claim 6, wherein the nucleotide sequence which causes readthrough is UAGCAAUUA or the corresponding DNA sequence TAGCAATTA, UAACAAUUA or the corresponding DNA sequence TAACAATTA, UGACAAUUA or the corresponding DNA sequence TGACAATTA, or UAGCARYYA or the corresponding DNA sequence TAGCARYYA, wherein italicized lettering indicates a stop codon, R is A or G, and Y is C, U or T.

8. The plasmid according to claim 6, wherein the promoter is the PM promoter or the T7 promoter.

9. A process for systemically expressing a fusion protein of a coat protein and a foreign protein in a plant comprising the steps of:

(a) inoculating a plant with a plant virus vector, wherein the plant virus vector comprises a viral assembly origin and a foreign protein gene linked downstream of a coat protein gene of a Tobamovirus via a nucleotide sequence of a Tobamovirus which causes readthrough, such that upon expression of the vector in the plant, the coat protein and the fusion protein are systemically produced in the plant; and (b) expressing the fusion protein systemically in the plant.

10. The process according to claim 9, wherein a part of the coat protein gene is lacking or replaced.

11. The process according to claim 9 wherein the nucleotide sequence which causes readthrough is UAGCAAUUA or the corresponding DNA sequence TAGCAATTA, UAACAAUUA or the corresponding DNA sequence TAACAATTA, UGACAAUUA or the corresponding DNA sequence TGACAATTA, or UAGCARYYA or the corresponding DNA sequence TAGCARYYA, wherein italicized lettering indicates a stop codon, R is A or G, and Y is C, U or T.

12. The process according to claim 9, wherein the plant is tobacco or tomato.

13. A process for producing a fusion protein of a coat protein and a foreign protein in a plant comprising the steps of:

(1) inoculating a plant with a plant virus vector, wherein the plant virus vector comprises a viral assembly origin and a foreign protein gene linked downstream of a coat protein gene of a Tobamovirus via a nucleotide sequence of a Tobamovirus which causes readthrough, such that upon expression of the vector in a plant, the coat protein and the fusion protein of the coat protein and the foreign protein are systemically produced in the plant;

(2) recovering virions from the plant; and (3) isolating the fusion protein from the virions.

14. The plant virus vector according to claim 2, wherein the coat protein gene has the sequence of SEQ ID NO:5.

15. The plant virus vector according to claim 2, wherein the coat protein gene has the sequence of SEQ ID NO:7.

16. A virion particle comprising a coat protein of a Tobamovirus and a fusion protein of the coat protein and a foreign protein.

17. A process for systemically expressing a fusion protein of a coat protein of a Tobamovirus and a foreign protein in a plant comprising the steps of:

(a) inoculating a plant with a plant virus vector, such that upon expression of the vector in a plant, the coat protein of a Tobamovirus and the fusion protein of the coat protein and the foreign protein are systemically produced in the plant; and (b) expressing the fusion protein systemically in the plant.

18. A tobacco mosaic viral (TMV) vector comprising a TMV assembly origin and a foreign protein gene linked downstream of a TMV coat protein gene via a TMV nucleotide readthrough sequence, such that upon expression of the vector in a plant, the TMV coat protein and a fusion protein of the coat protein and the foreign protein are systemically produced in the plant, wherein said readthrough sequence is from a 130/180K protein gene, UAGCAAUUA or the corresponding DNA sequence TAACAATTA, UAACAAUUA or the corresponding DNA sequence TAACAATTA, UGACAAUUA or the corresponding DNA sequence TGACAATTA, or UAGCARYYA or the corresponding DNA sequence TAGCARYYA, wherein italicized lettering indicates a stop codon, R is A or G, and Y is C, U or T.

19. The vector according to claim 18, wherein a part of the coat protein gene is lacking or replaced.

20. A plasmid comprising the plant virus vector of claim 18.

21. The plasmid according to claim 20, wherein the plasmid further comprises a promoter, wherein said promoter is the PM promoter or the T7 promoter.

22. A process for systemically expressing a fusion protein of a TMV coat protein and a foreign protein in a plant comprising the steps of:

(a) inoculating a plant with a TMV vector comprising a TMV assembly origin and a foreign protein gene linked downstream of a TMV coat protein gene via a TMV readthrough sequence, such that upon expression of the vector in the plant, the TMV coat protein and the fusion protein are systemically produced in the plant, wherein said readthrough sequence is from a 130/180K protein gene, UAGCAAUUA or the corresponding DNA sequence TAGCAATTA, UAACAAUUA or the corresponding DNA sequence TAACAATAA, TGACAAUUA or the corresponding DNA sequence TGACAATTA, or UAGCARYYA or the corresponding DNA sequence TAGCARYYA, wherein italicized lettering indicates a stop codon, R is A or G, and Y is C, U or T, and (b) expressing the fusion protein systemically in the plant.

23. The process according to claim 22, wherein a part of the coat protein gene is lacking or replaced.

24. A process for producing a fusion protein of a TMV coat protein and a foreign protein in a plant comprising the steps of:

(1) inoculating a plant with a TMV vector comprising a TMV assembly origin and a foreign protein linked downstream of a TMV coat protein gene via a readthrough sequence, such that upon expression of the vector in the plant, the TMV coat protein and a fusion protein of the coat protein and the foreign protein are systemically produced in the plant, wherein said readthrough sequence is from a 130/180K protein gene, UAGCAAUUA or the corresponding DNA sequence TAGCAATTA, UAACAAUUA or the corresponding DNA sequence TAACAATAA, TGACAAUUA or the corresponding DNA sequence TGACAATTA, or UAGCARYYA or the corresponding DNA sequence TAGCARYYA, wherein italicized lettering indicates a stop codon, R is A or G, and Y is C, U or T;

(2) recovering virions from the plant; and (3) isolating the fusion protein from the virions.

25. The process according to claim 24, wherein a part of the coat protein gene is lacking or replaced.

* * * * *